United States Patent
Gurny et al.

(10) Patent No.: US 9,155,745 B2
(45) Date of Patent: Oct. 13, 2015

(54) BEVACIZUMAB FORMULATIONS WITH LOWER AGGREGATION PROPENSITY, COMPRISING CORTICOSTEROID ANTI-INFLAMMATORY DRUGS

(75) Inventors: Robert Gurny, Geneva (CH); Cinzia Stella, Geneva (CH); Cyrus Tabatabay, Bernex (CH); Marieke Veurink, Geneva (CH); Constantin Pournaras, Conches (CH)

(73) Assignee: UNIVERSITE DE GENEVE, Geneva (CH)

( * ) Notice: Subject to any disclaimer, the term of this patent is extended or adjusted under 35 U.S.C. 154(b) by 465 days.

(21) Appl. No.: 12/797,166

(22) Filed: Jun. 9, 2010

(65) Prior Publication Data

US 2010/0316638 A1 Dec. 16, 2010

Related U.S. Application Data

(60) Provisional application No. 61/187,287, filed on Jun. 16, 2009.

(51) Int. Cl.
*A61K 39/395* (2006.01)
*A61K 31/56* (2006.01)
*A61K 31/573* (2006.01)
*A61K 45/06* (2006.01)

(52) U.S. Cl.
CPC ........... *A61K 31/573* (2013.01); *A61K 39/3955* (2013.01); *A61K 39/39591* (2013.01); *A61K 45/06* (2013.01)

(58) Field of Classification Search
None
See application file for complete search history.

(56) References Cited

U.S. PATENT DOCUMENTS

2009/0092650 A1* 4/2009 Warren et al. .................. 424/422
2009/0226422 A1* 9/2009 Chaudhary et al. ......... 424/130.1
2010/0098691 A1* 4/2010 Goh et al. .................. 424/133.1
2011/0097340 A1* 4/2011 Ramachandra et al. ... 424/158.1
2013/0017197 A1    1/2013 Gurny et al.
2013/0028920 A1    1/2013 Gurny et al.
2013/0131190 A1    5/2013 Moeller et al.

OTHER PUBLICATIONS

Veurink et al., European Journal of Pharmaceutics and Biopharmaceutics 78: 271-277, 2011.*

Westermaier et al., European Journal of Pharmaceutics and Biopharmaceutics 85: 773-780, 2013.*
Ahmadieh, H. et al. "Intravitreal bevacizumab with or without triamcinolone for refractory diabetic macular edema; a placebo-controlled, randomized clinical trial" *Graefes Arch Clin. Exp. Ophthalmol.*, 2008, pp. 483-489, vol. 246.
Andreoli, C. M. et al. "Anti-vascular endothelial growth factor therapy for ocular neovascular disease" *Curr. Opin. Ophthalmol.*, 2007, pp. 502-508, vol. 18.
Augustin, A. J. et al. "Triple Therapy for Choroidal Neovascularization Due to Age-Related Macular Degeneration" *Retina*, 2007, pp. 133-140, vol. 27.
Colucciello, M. "Intravitreal Bevacizumab and Triamcinolone Acetonide Combination Therapy for Exudative Neovascular Age-Related Macular Degeneration: Short-Term Optical Coherence Tomography Results" *Journal of Ocular Pharmacology and Therapeutics*, 2008, pp. 15-24, vol. 24, No. 1.
Presta, L. G. et al. "Humanization of an Anti-Vascular Endothelial Growth Factor Monoclonal Antibody for the Therapy of Solid Tumors and Other Disorders" *Cancer Research*, Oct. 15, 1997, pp. 4593-4599, vol. 57.
Veurink, M. et al. "In-vitro stability of bevacizumab (Avastin®) and ranibizumab (Lucentis®) in combination with anti-inflammatory drugs for ophthalmological applications" Swiss Pharma Day, Oct. 9, 2008, p. 1-2, poster and abstract only.
Veurink, M. et al. "In-Vitro Stability of Avastin and Lucentis in Combination with Anti-Inflammatory Drugs for Ophthalmological Applications" *Swiss Pharma*, Dec. 2008, pp. 1-44, see P-6 Poster Session-Abstracts on p. 18.
Veurink, M. et al. "Association of ranibizumab (Lucentis®) or bevacizumab (Avastin®) with dexamethasone and triamcinolone acetonide: An in vitro stability assessment" *European Journal of Pharmaceutics and Biopharmaceutics*, 2011, pp. 271-277, vol. 78.
Veurink, M. et al. "Breaking the Aggregation of the Monoclonal Antibody Bevacizumab (Avastin®) by Dexamethasone Phosphate: Insights from Molecular Modelling and Asymmetrical Flow Field-Flow Fractionation" *Pharmaceutical Research*, 2012, pp. 1-12.
Vazquez-Rey, M. et al. "Aggregates in Monoclonal Antibody Manufacturing Processes" *Biotechnology and Bioengineering*, Jul. 2011, pp. 1494-1508, vol. 108, No. 7.
Kayser, V. et al. "Evaluation of a Non-Arrhenius Model for Therapeutic Monoclonal Antibody Aggregation" *Journal of Pharmaceutical Sciences*, Jul. 2011, pp. 2526-2542, vol. 100, No. 7.
Nabih, M. et al. "Toxicity of high-dose intravitreal dexamethasone" *International Ophthalmology*, 1991, pp. 233-235, vol. 15.
Currently pending claims of U.S. Appl. No. 13/637,041, 2014.
Currently pending claims of U.S. Appl. No. 13/637,051, 2015.
Currently pending claims of U.S. Appl. No. 13/811,986, 2014.

* cited by examiner

*Primary Examiner* — Phillip Gambel
(74) *Attorney, Agent, or Firm* — Saliwanchik, Lloyd & Eisenschenk

(57) ABSTRACT

The present invention is directed to combination formulations of monoclonal antibodies with anti-inflammatory agents, related methods and uses thereof.

19 Claims, 3 Drawing Sheets

BEVACIZUMAB FORMULATIONS WITH LOWER AGGREGATION PROPENSITY, COMPRISING CORTICOSTEROID ANTI-INFLAMMATORY DRUGS

CROSS-REFERENCE TO RELATED APPLICATION

This application claims the benefit of U.S. Provisional Application Ser. No. 61/187,287, filed Jun. 16, 2009, the disclosure of which is hereby incorporated by reference in its entirety, including all figures, tables and amino acid or nucleic acid sequences.

FIELD OF THE INVENTION

The present invention is directed to combination formulations of monoclonal antibodies with anti-inflammatory agents, more particularly with corticosteroid anti-inflammatory agents, and uses thereof.

BACKGROUND OF THE INVENTION

Progresses in gene recombinant technology have enabled the large scale production of physiologically active proteins such as monoclonal antibodies for diagnostic and therapeutic applications. The recent development of humanized monoclonal antibodies has spawned an unprecedented interest in using these molecules as therapeutics since they can specifically target disease implicated molecules, thus essentially side-stepping the secondary effects that are usually associated with conventional drug therapies. Therapeutic monoclonal antibodies have thus become the fastest growing area of biopharmaceutical applications.

While the production and purification scales have reached industrial levels, there are novel concerns about strategies for their stable formulation and delivery. Physical and chemical instability of antibodies is really a complex function of solution conditions and temperature. Antibodies are for example susceptible to deamidation, isomerization, oxidation, proteolysis, aggregation and other covalent modifications. However, unlike other model proteins, antibody stability is not necessarily dependent on protein concentration, buffer concentration, salt concentration, or agitation. Some antibodies can be stabilized by changing different parameters in the formulation, like pH, excipients and buffer, though. However, antibody stabilization is a hard task as their activity is very sensitive to environment conditions which render it very difficult to predict, notably because each antibody has a very specific and characteristic stability profile. The lack of effect for primary factors commonly known to affect physical stability suggests that the mechanism of antibody stability is counter intuitive and unlike other proteins. Further, those aggregation phenomena are suspected to result in potential clinical side-effects or toxicity since aggregates can reduce the efficacy and enhance the immunogenicity of the protein drug (Demeule et al., 2006, *Eur. J. Pharm. Biopharm.*, 62:121-30).

Antibody aggregation is also a source of batch to batch variabilities in the antibody production chain and its control leads to regulatory and quality control burden which have extremely costly consequences.

Further, aggregation propensity of antibodies affects their stability in storage, including shelf-life and their useable administration time, once removed from optimum storage conditions.

Bevacizumab (Avastin®) is a recombinant monoclonal humanized IgG1 antibody with a molecular weight of 149 kDa that binds to and inhibits the biologic activity of vascular endothelial growth factor (VEGF) which has been approved for the treatment of metastatic cancer of the colon or rectum. Currently, bevacizumab is widely used off-label for the treatment of neovascular age-related macular degeneration (AMD), a common form of progressive age-related vision loss (Andreoli et al., 2007, *Curr. Opin. Opthalmol.*, 18:502-8), by intraocular injection. This off-label use was introduced after Ranibizumab (Lucentis®), a humanized monoclonal antibody fragment derived from the same murine antibody precursor as bevacizumab with a molecular weight of 48 kiloDalton (kDa) had been registered in 2006 for the treatment of AMD. For ranibizumab, a monthly injection into the vitreous cavity is recommended to maintain therapeutically effective drug concentrations (Regillo et al., 2008, *Am. J. Opthalmol.*, 145, 239-48) and the same frequency is generally reported for bevacizumab injections. Nevertheless, a reduced frequency of injections would be favourable because of patient discomfort and risk of complications (Brown et al., 2007, *Am. J. Opthalmol.*, 144:627-37).

Several clinical trials have reported the administration of both bevacizumab and some anti-inflammatory drugs such as triamcinolone acetonide or dexamethasone in the treatment of neovascular age-related macular degeneration through separate intravitreal injections of the two drugs in order to address the multifactorial pathogenesis of AMD (Augustin et al., 2007, *Retina*, 27, 133-40; Ahmadieh et al., 2008, *Graefes Arch. Clin. Exp. Opthalmol.*, 246(4):483-9; Colucciello et al., 2008, *J. Ocul. Pharmacol. Ther., February;* 24(1):15-24).

Among one of the advantages that promoted the off-label use of bevacizumab is its much lower price as compared to its fragment ranibizumab that lacks an Fc portion. However, bevacizumab, which is an intact antibody, presents, as such, the significant aggregation propensity commonly found for antibodies mentioned above. Surface active agents like polysorbate 20 and 80 which are widely used to reduce the rate of protein aggregation are also used in the formulation of AVASTIN where 0.04% of polysorbate 20 is present. However, surface active agents can only be used in antibodies formulations at percentages of 0.01% to 0.05% because of their participation in protein unfolding at higher concentrations.

Since aggregation is a major issue for the production, formulation and/or stability of therapeutic antibodies since antibody aggregates can lead to loss of biological activity, loss of solubility and even increased immunogenicity the development of a method of preparation and/or formulations of antibodies that would lead to a longer shelf-life and stability of those antibodies would be highly desirable.

SUMMARY OF THE INVENTION

The invention relates to the unexpected finding of the stabilizing effects of corticosteroid anti-inflammatory drugs such as dexamethasone and betamethasone on intact antibodies such as bevacizumab when formulated in liquid solution, notably as a combination formulation suitable for administration to a mammal. The invention further relates to the unexpected finding of the stabilizing effects of corticosteroid anti-inflammatory drugs such as dexamethasone and betamethasone on intact antibodies such as bevacizumab when used even at very low concentrations in a process for the preparation of such intact antibodies. Stabilization of intact antibodies such as bevacizumab is supported in particular by the observed reduced propensity of bevacizumab to form aggregates and the reverting of already formed aggregates of bevacizumab into an essentially monomeric state. The invention further relates to the surprising finding of stabilized combination formulations of bevacizumab with corticosteroid anti-inflammatory drugs such as dexamethasone and betamethasone, which have an increased shelf-life as compared to known formulations of bevacizumab.

A first aspect of the invention provides a stable antibody combination formulation, said formulation comprising an aqueous carrier, an intact antibody and a corticosteroid anti-inflammatory drug.

A second aspect of the invention provides a pharmaceutical formulation such as a formulation formulated for administration to a mammal (e.g. human) comprising a stable antibody combination formulation according to the invention or a stabilized antibody according to the invention.

A third aspect of the invention provides a pharmaceutical unit dosage form suitable to a mammal comprising formulation according to the invention.

A fourth aspect of the invention provides a kit comprising in one or more container(s) a formulation according to the invention together with instruction of use of said formulation.

A fifth aspect of the invention provides a formulation according the invention for use as a medicament.

A sixth aspect of the invention provides a formulation according the invention for the is prevention or treatment of a disease or a disorder selected from a cancer, a neovascular age-related macular degeneration disease (AMD) and a disorder associated with AMD.

A seventh aspect of the invention provides a method of stabilizing an intact antibody in aqueous solution.

An eighth aspect of the invention provides a process for the preparation of an intact antibody in aqueous solution or a formulation thereof according to the invention.

A ninth aspect of the invention provides a stabilized intact antibody or a formulation thereof obtainable by a process or a method according to the invention.

A tenth aspect of the invention provides a method of preventing, treating or ameliorating a disease or a disorder selected from a cancer, a neovascular age-related macular degeneration disease (AMD) and a disorder associated with AMD, said method comprising administering in a subject in need thereof a prophylactic or therapeutically effective amount of a formulation according to the invention or of a stabilized intact antibody according to the invention.

An eleventh aspect of the invention provides a use of a formulation according to the invention or of a stabilized intact antibody according to the invention for the preparation of a pharmaceutical formulation for the prevention and/or treatment of a disorder selected from a cancer, a neovascular age-related macular degeneration disease (AMD) and a disorder associated with AMD.

DETAILED DESCRIPTION OF THE INVENTION

Figure 1A:
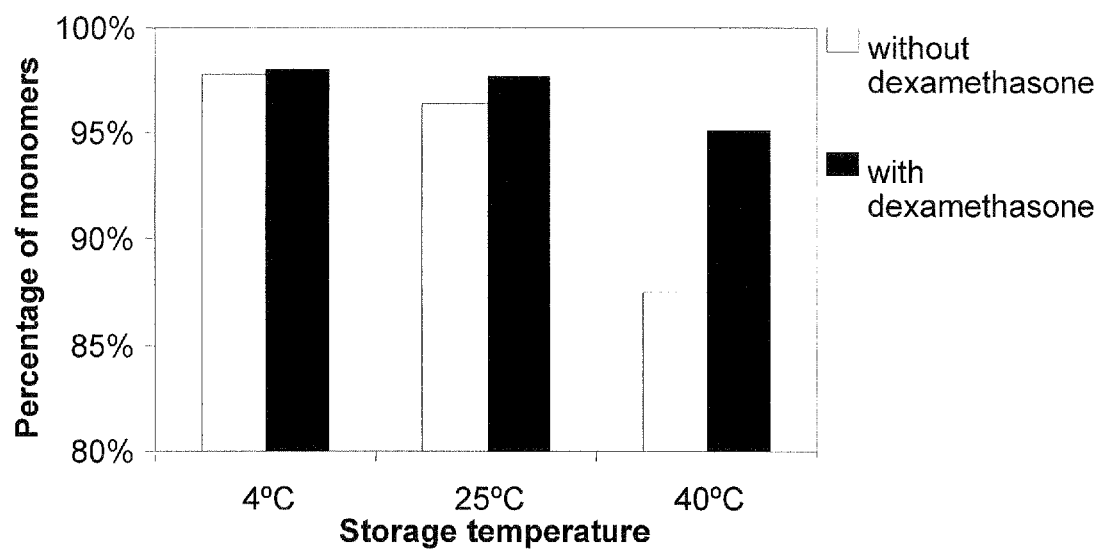
FIGS. 1A and 1B show the stabilizing effect of dexamethasone on bevacizumab expressed in Percentage of bevacizumab monomers after 35 days of storage at different temperatures in phosphate buffer at 50 mM. 1A: at pH 6.2; 1B: at pH 7.0 (white: bevacizumab alone; black: bevacizumab combined with dexamethasone at a bevacizumab:dexamethasone molar ratio of 1:153), according to the protocol described in Example 1.

The term "intact monoclonal antibody" refers to monoclonal antibodies which possess both Fab and Fc regions as opposed to Fab or Fab2 fragments. Intact monoclonal antibodies according to the invention present an aggregation propensity. In a particular embodiment, an intact antibody according to the invention is bevacizumab, notably AVASTIN such as described in Presta et al., *Cancer Res.,* 57 (1997), 4593-4599.

The term "corticosteroid anti-inflammatory drug" includes dexamethasone, dexamethasone sodium phosphate and the like, betamethasone, betamethasone sodium phosphate and the like, flumethasone, fluorometholone, fluprednisolone, cortisol 21-phosphate, paramethasone disodium phosphate, methylprednisolone sodium phosphate, prednisolone sodium phosphate and hydrocortisone sodium phosphate. In a particular embodiment, a corticosteroid anti-inflammatory drug according to the invention is dexamethasone or a derivative thereof. In another particular embodiment, a corticosteroid anti-inflammatory drug according to the invention is dexamethasone or a derivative thereof of Formula (I):

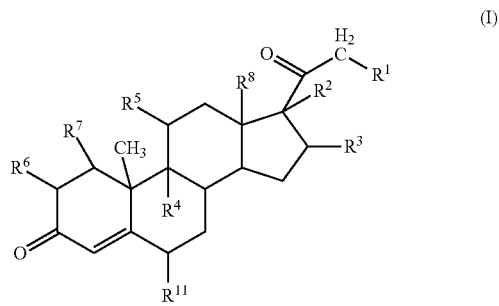

wherein $R^1$ is selected from H, halogen, —OH, —O$_4$PHNa$_2$, —O—C(O)—$R^9$, $R^2$ is selected from H, OH, —O—C(O)—$R^{10}$, $R^3$ is selected from H or —CH$_3$, $R^4$ is selected from H, halogen such as fluoro, chloro, $R^5$ is selected from H, OH and carbonyl, $R^6$ and $R^7$ are H or form together a double bond, $R^8$ is selected from optionally substituted optionally substituted $C_1$-$C_6$ alkyl such as optionally substituted methyl and optionally substituted acetyl, $R^9$ and $R^{10}$ are independently selected from optionally substituted $C_1$-$C_6$ alkyl such as optionally substituted methyl and optionally substituted ethyl and optionally substituted $C_3$-$C_8$-cycloalkyl, $R^{11}$ is selected from H or optionally substituted $C_1$-$C_6$ alkyl such as optionally substituted methyl, or a pharmaceutically acceptable salt thereof.

In a particular embodiment, a corticosteroid anti-inflammatory drug according to the invention is selected from dexamethasone, betamethasone, or a pharmaceutically acceptable salt thereof. In a particular embodiment, a corticosteroid anti-inflammatory drug according to the invention is selected from dexamethasone sodium phosphate or betamethasone sodium phosphate. The term "dexamethasone" is used herein to refer to dexamethasone in the form of the free acid or in the form of a pharmaceutically acceptable salt or ester thereof, such as dexamethasone sodium phosphate. The term "betamethasone" is used herein to refer to betamethasone in the form of the free acid or in the form of a pharmaceutically acceptable salt or ester thereof, such as betamethasone sodium phosphate.

The term "alkyl" when used alone or in combination with other terms, comprises a straight chain or branched $C_1$-$C_6$ alkyl which refers to monovalent alkyl groups having 1 to 6 carbon atoms. This term is exemplified by groups such as methyl, ethyl, n-propyl, i-propyl, n-butyl, s-butyl, i-butyl, t-butyl and the like.

The term "$C_3$-$C_8$-cycloalkyl" refers to a saturated carbocyclic group of from 3 to 8 carbon atoms having a single ring or multiple condensed rings. $C_3$-$C_8$-cycloalkyl includes cyclopropyl, cyclobutyl and the like.

The term "derivative" refers to any compound the addition of which to the intact antibody, is capable of providing directly or indirectly, the activity disclosed herein.

The term "age-related macular degeneration" (AMD) includes an eye progressive disease presenting an onset usually after age 60 that progressively destroys the macula, the central portion of the retina, impairing central vision. AMD rarely causes complete blindness because only the center of vision is affected. However, injury to the macula in the center of the retina impair the ability to see straight ahead clearly impairing reading, driving, or perform other daily activities requiring central vision. AMD reduces autonomy and increases the risks of falling in the elderly. In the very early stages, AMD usually causes no symptoms but a blurred or fuzzy vision, which may appear in one eye, or both, may be an early sign of AMD that, in some cases, might become less apparent under brighter lighting conditions. Further main symptoms are the appearance of straight lines as wavy or crooked (in particular in wet AMD), a decreased contrast sensitivity and ability to color distinction, an empty or dark growing area in the center of vision. Dry AMD is the most common type and occurs when light-sensitive cells in the macula degrade and central vision begins to slowly fade. Early AMD, the first stage, has a presence of drusens, yellow deposits under the retina, but usually no vision loss or problem is detected. In Intermediate AMD, many medium sized drusens or large sized drusens are observed and blurry areas rendering more difficult to perform regular tasks. In advanced dry AMD, the light-sensitive cells begin to degrade dramatically and a blurred spot generally appear in the central of vision. Dry AMD can evolve into wet AMD which is more severe and where vision loss occurs more rapidly. In wet AMD, small, abnormal thin and fragile blood vessels form and begin to break and leak. The blood and fluids eventually causes damage to the macula and causes rapid loss in vision. Although wet AMD is less common, loss of vision occurs faster in this case so it is essential to get it diagnosed and efficiently treated as quickly as possible.

The term "cancer" includes metastatic and non-metastatic cancers such as colon cancer, rectal cancer, breast cancer, renal cell carcinoma, glioblastoma multiforme, ovarian cancer, prostate cancer, liver cancer, pancreatic cancer or other cancers responsive to the inhibition of angiogenesis.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it such as a preventive early asymptomatic intervention; (b) inhibiting the disease, i.e., arresting its development; or relieving the disease, i.e., causing regression of the disease and/or its symptoms or conditions such as improvement or remediation of damage. In particular, the methods, uses, formulations and compositions according to the invention are useful in the preservation of vision and/or prevention of vision loss in patients with age-related macular degeneration and/or in the treatment of cancers.

The term "subject" as used herein refers to mammals. For examples, mammals contemplated by the present invention include human, primates, domesticated animals such as cattle, sheep, pigs, horses, laboratory rodents and the like.

The term "effective amount" as used herein refers to an amount of at least one polypeptide or a pharmaceutical formulation thereof according to the invention that elicits the biological or medicinal response in a tissue, system, animal or human that is being sought. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active polypeptide sufficient to reduce the progression of the disease, notably to reduce or inhibit the destruction process of the macula and/or prevent the progress of central vision loss and/or to lead to an amelioration of AMD related symptoms and thereby elicit the response being sought (i.e. an "inhibition effective amount").

The term "efficacy" of a treatment according to the invention can be measured based on changes in the course of disease in response to a use or a method according to the invention. For example, the efficacy of a treatment of a AMD related disorder according to the invention can be measured by a reduction of vision loss and/or by a protective effect against macular degeneration and the like associated with AMD related macular degeneration and/or destruction. Those effects can be measured by an amelioration of visual acuity and a decrease in retinal thickness such as described in Leydolt et al., 2009, *Acta Opthalmol.*, May 22, which should also exert a positive influence on central vision dysfunctions typically observed in the AMD patients. The efficacy of a treatment of a cancer according to the invention can be measured by a reduction of tumor volume, and/or an increase of progression free survival time.

The term "pharmaceutical formulation" refers to preparations which are in such a form as to permit biological activity of the active ingredient(s) to be unequivocally effective and which contain no additional component which would be toxic to subjects to which the said formulation would be administered.

The term "stable" or "stabilized" refers in the context of the invention to formulations in which the antibody therein retains its physical stability (e.g. level of aggregation or aggregation propensity decreased, absence of precipitation or denaturation) and/or chemical stability (e.g. absence of chemically altered forms) upon storage. Stability of the antibody formulations according to the invention may be measured by various techniques known to the skilled person in the art. For example, stability can be measured by aggregation state measurements (e.g. by MALS after separation by AFFF, high performance size exclusion, fluorescence microscopy, electron microscopy). Preferably, the stability of the formulation is measured at a selected temperature and/or for a selected period of time storage. Typically, the stability of a formulation according to the invention is measured at T 40° C. for a period of 35 days.

Formulations According to the Invention

According to an embodiment, is provided a stable antibody combination formulation, said formulation comprising an aqueous carrier, an intact antibody and a corticosteroid anti-inflammatory drug.

According to another embodiment, is provided a stabilized antibody or a formulation thereof obtainable by a process or a method according to the invention.

According to another further embodiment, is provided a stable antibody formulation according to the invention wherein the intact antibody is bevacizumab.

According to further embodiment, the invention provides a formulation according to the invention wherein bevacizumab or is at a concentration in the range from about 5 mg/ml to about 100 mg/ml.

According to another further embodiment, the invention provides a formulation according to the invention wherein the corticosteroid anti-inflammatory drug is at a concentration in the range from about 0.1 mg/ml to about 13 mg/ml.

According to another further embodiment, the invention provides a formulation according to the invention wherein the molar ratio corticosteroid anti-inflammatory drug to bevacizumab is in the range from about 1:1 to about 200:1.

According to another further embodiment, is provided a stabilized antibody formulation according to the invention wherein the corticosteroid anti-inflammatory drug is dexamethasone or a derivative thereof.

According to another further embodiment, the invention provides a formulation according to the invention wherein the corticosteroid anti-inflammatory drug is dexamethasone.

According to another further embodiment, the invention provides a formulation according to the invention wherein the corticosteroid anti-inflammatory drug is betamethasone.

According to another further embodiment, the invention provides a formulation according to the invention wherein the formulation has a pH in the range between about 4.5 and about 7.5.

According to another further embodiment, the invention provides a formulation according to the invention further comprising an excipient.

According to another further embodiment, the invention provides a formulation according to the invention wherein less than 10% of bevacizumab forms an aggregate as determined by MALS coupled to AFFF during storage at 40° C. for 35 days.

According to further embodiment, the invention provides a formulation according to the invention wherein the formulation is a pharmaceutical formulation, notably formulated for administration in a mammal, typically a human mammal.

According to further embodiment, the invention provides a formulation according to the invention wherein the formulation is a pharmaceutical formulation suitable for injection in human (e.g. intravitreous or intravenous).

According to further embodiment, the invention provides a formulation according to the invention wherein the formulation is a pharmaceutical formulation suitable for ocular injection in human (e.g. intravitreous).

According to further embodiment, the invention provides a formulation according to the invention wherein the formulation is a pharmaceutical formulation suitable for intravenous injection in human.

According to another further embodiment, the invention provides a pharmaceutical unit dosage form suitable for ocular administration to a mammal comprising an antibody formulation according the invention in a suitable container.

According to another further embodiment, the invention provides a kit comprising in one or more container a formulation according to the invention together with instruction of use of said formulation.

According to another further embodiment, the invention provides a formulation according for use as a medicament.

According to another further embodiment, the invention provides a formulation according the invention for the prevention or treatment of a disease or a disorder selected from a cancer, a neovascular age-related macular degeneration disease (AMD) and a disorder associated with AMD.

Compositions or formulations according to the invention may be administered as a pharmaceutical formulation which can contain one or more intact antibody according to the invention in any form described herein. Formulations of this invention may further comprise one or more pharmaceutically acceptable additional ingredient(s) such as alum, stabilizers, antimicrobial agents, buffers, coloring agents, flavoring agents, adjuvants, and the like.

Formulations of the invention, together with a conventionally employed adjuvant, carrier, diluent or excipient may be placed separately into the form of pharmaceutical compositions and unit dosages thereof, and in such form may be employed as liquids such as solutions, suspensions, emulsions, elixirs, or capsules filled with the same, all in the form of sterile injectable solutions for ocular (including intra-vitreous cavity) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Such liquid preparations may contain additives including, but not limited to, suspending agents, emulsifying agents, non-aqueous vehicles and preservatives. Suspending agent include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Injectable compositions are typically based upon injectable sterile saline or phosphate-buffered saline or other injectable carriers known in the art.

In another particular aspect, the formulation is adapted for delivery by repeated administration.

In another aspect, a particular advantage of formulations according to the invention is that the corticosteroid drug not only stabilizes the intact antibody formulation but also exert an additional beneficial therapeutic effect as compared to the said intact antibody alone.

Further materials as well as formulation processing techniques and the like are set out in *Part 5 of Remington's*

*Pharmaceutical Sciences*, 21st Edition, 2005, University of the Sciences in Philadelphia, Lippincott Williams & Wilkins, which is incorporated herein by reference.

Formulations according to the invention, stabilized intact antibodies and formulations thereof obtainable by a process or a method according to the invention are useful in the prevention and/or treatment of a disease or a disorder such as for example in the case of stabilized in the treatment of a disease or a disorder selected from AMD, in particular in the prevention and/or treatment of AMD related disorders such as macular degeneration and progressive vision loss and cancers.

Methods of Preparation According to the Invention

According to one aspect of the invention, is provided a method of stabilizing an intact antibody in aqueous solution by combining said intact antibody with a corticosteroid anti-inflammatory drug.

According to another embodiment, is provided a process for the preparation of an intact antibody or a formulation thereof comprising the steps of:

(i) combining said intact antibody with a cortico steroid anti-inflammatory drug into a liquid mixture or forming said intact antibody in a liquid medium containing a corticosteroid anti-inflammatory drug;

(ii) collecting the liquid mixture or liquid medium obtained under step (i) containing the stabilized intact antibody wherein the percentage of monomers of intact antibody is increased as compared to intact antibody prepared in absence of the said corticosteroid anti-inflammatory drug. Typically, the percentage of monomers of stabilized intact antibody is of about at least 90% after 35 days at 40° C. at 25 mg/ml.

In a particular embodiment, is provided a method according to the invention wherein the said intact antibody is bevacizumab. For example, bevacizumab used in a method or process according to the invention may be obtained by a process as described in Presta et al., 1997, above.

In a further embodiment, the invention provides a method or a process according to the invention wherein the aqueous solution is a pharmaceutical formulation and the intact antibody is in a therapeutically effective amount. Typically, in the case of bevacizumab for AMD treatment the therapeutically effective amount of AVASTIN is from about 5 mg/ml to about 100 mg/ml. Typically, in the case of bevacizumab for cancer treatment, the therapeutically effective amount of AVASTIN is from about 10 mg/ml to 50 mg/ml.

In a further aspect of the invention, the method or process according to the invention may be useful in decreasing the aggregation ability of an intact antibody during its production process and/or in rescuing production batches containing already aggregated antibodies by reverting them into an essentially monomeric state. In this case, the concentration of corticosteroid anti-inflammatory drug may be present at a sub-therapeutic concentration, in the antibody medium (e.g. about 1 mg/ml). Optionally, the method or process according to the invention may further comprise a step of dialyzing out the corticosteroid anti-inflammatory drug when used at a sub-therapeutic concentration. Typically, a process for the preparation of an intact antibody or a formulation thereof according to the invention may comprise a further step (iii) of dialyzing out the corticosteroid anti-inflammatory drug when used at a sub-therapeutic concentration during or after the collection step (ii).

In another aspect the method or process according to the invention may be useful in preparing stable formulations of intact antibodies presenting an increased shelf-life and enabling multiple dosing conditioning.

In a particular embodiment, is provided a method or process according to the invention wherein the said corticosteroid anti-inflammatory drug is dexamethasone or a derivative thereof.

In a particular embodiment, is provided a method or process according to the invention wherein the said corticosteroid anti-inflammatory drug is dexamethasone.

In a particular embodiment, is provided a method or process according to the invention wherein the said corticosteroid anti-inflammatory drug is betamethasone.

Mode of Administration

Formulations of this invention may be administered in any manner including parenterally, transdermally, rectally, transmucosally, intra-ocular or combinations thereof. Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well as a slow controlled i.v. infusion.

Intraocular administration includes, but is not limited to, injection into the vitreous humour, subconjunctival, sub-tenon, topical applications. The formulations of this invention may also be administered in the form of an ocular implant, which allows slow release of the compositions.

Methods According to the Invention

According to another aspect, the invention provides a method of preventing, treating or ameliorating a neovascular age-related macular degeneration or a disorders associated with AMD, said method comprising administering in a subject in need thereof a prophylactic or therapeutically effective amount of a stable bevacizumab formulation or a formulation of a stabilized bevacizumab obtainable by a process or a method according to the invention.

Typically, for AMD treatment the therapeutically effective dose of a stabilized bevacizumab according to the invention is from about 1.0 mg to 2.5 mg per eye.

According to another aspect, the invention provides a method of preventing, treating or ameliorating a cancer, said method comprising administering in a subject in need thereof a prophylactic or therapeutically effective amount of a stabilized antibody formulation or a formulation of a stabilized bevacizumab according to the invention.

Typically, for cancer treatment such as colorectal cancer, the therapeutically effective dose of a stabilized bevacizumab according to the invention is from about 3 mg/kg body weight to about 20 mg/kg body weight.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Patients

In an embodiment, patients according to the invention are patients suffering from a disease selected from cancer and age-related macular degeneration (AMD).

In a particular embodiment, patients according to the invention are suffering from age-related macular degeneration (AMD), including early, intermediate and late stage AMD.

In a particular embodiment, patients according to the invention are suffering from early stage AMD.

In a particular embodiment, patients according to the invention are suffering from dry AMD.

In a particular embodiment, patients according to the invention are suffering from wet AMD.

In a particular embodiment, patients according to the invention are suffering from a cancer.

In a particular embodiment, patients according to the invention are suffering from a metastatic cancer selected from colon or rectal cancer.

References cited herein are hereby incorporated by reference in their entirety. The present invention is not to be limited in scope by the specific embodiments and drawings described herein, which are intended as single illustrations of individual aspects of the invention, and functionally equivalent methods and components are within the scope of the invention. The examples illustrating the invention are not intended to limit the scope of the invention in any way.

EXAMPLES

General Procedures & Conditions

The following studies are conducted to support the influence of corticosteroid anti-inflammatory drugs such as dexamethasone on the stability of intact antibodies such as bevacizumab and the like. Monomer percentages of the intact antibody are measured to determine whether its association with the corticosteroid anti-inflammatory drugs into a single formulation influences the aggregation state of this protein. Since aggregates have been observed to cause severe side-effects, this study is of great importance for anticipating beneficial effects in clinical use.

The following abbreviations refer respectively to the definitions below:

mM (millimolar), nm (nanometers), AFFF (asymmetrical flow field-flow fractionation), MALS (multi-angle light scattering), UV (Ultraviolet).

Example 1

Comparison of the Stability of Bevacizumab Alone and in Combination with Dexamethasone Phosphate Three different series of samples were tested: Tests I. Commercial formulation of bevacizumab (AVASTIN, Roche Pharma, Reinach, Switzerland) was dialysed overnight into three different isotonic buffers to change the pH. A 50 mM acetate buffer pH 5.0, 50 mM phosphate buffer pH 6.2 and 50 mM phosphate buffer pH 7.0 were used. A phosphate buffer pH 6.2 was selected because this buffer is used in the commercial product AVASTIN. The buffer choice was based on a pH range and buffer capacity that is tolerated by the eye and that is acceptable for the stability of antibodies. After dialysis, bevacizumab at a concentration of 19 mg/ml (pH 5.0=19.8 mg/ml, Ph 6.2=19.2 mg/ml, pH 7.0=18.7 mg/ml) was combined with dexamethasone 21-phosphate disodium salt (Sigma-Aldrich, Lausanne, Switzerland) at a molar ratio of bevacizumab:dexamethasone=1:153. Both the antibody alone and the combined formulation were stored at 4° C., 25° C. and 40° C. during 35 days (FIGS. 1 and 2).

Figure 2A:
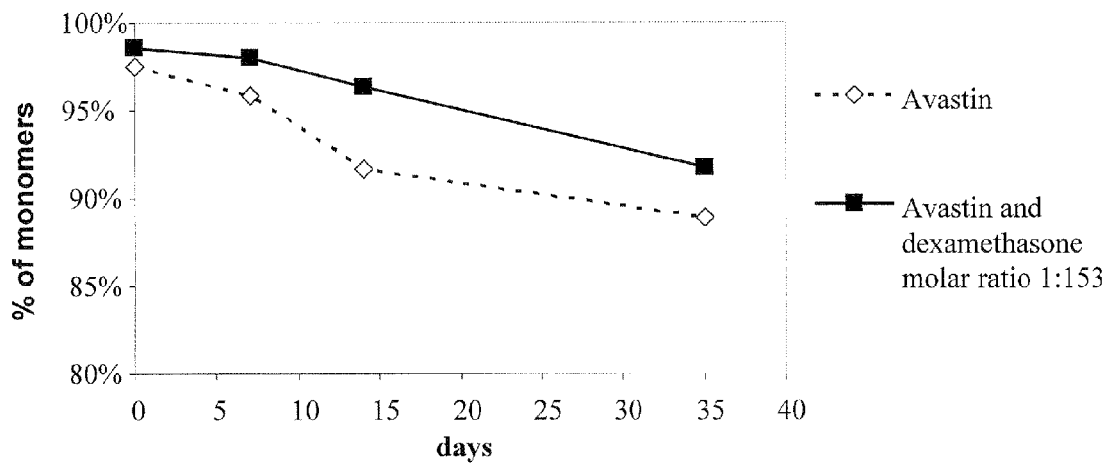
FIG. 2A shows the stabilizing effect of dexamethasone on bevacizumab, expressed in percentage of bevacizumab monomers, after combining the commercial product AVASTIN with dexamethasone when stored at 40° C., as described in Example 1. (2A: black line: AVASTIN alone; dotted line: AVASTIN associated with dexamethasone at a bevacizumab:dexamethasone molar ratio of 1:153).

Tests II. Dexamethasone was added as a solid form (in order to avoid inducing a change in the concentration of the antibody) to the commercial product of bevacizumab (AVASTIN), molar ratio bevacizumab:dexamethasone=1:153. Both the AVASTIN product alone, and the combined formulation were stored at 40° C. during 35 days. (FIG. 2A).

Tests III. Commercial formulation of bevacizumab (AVASTIN, Roche Pharma, Reinach, Switzerland) was dialysed overnight into pH 6.2 (see tests I). After dialysis, dexamethasone was added in three different concentrations, obtaining the following molar ratios:
  i. bevacizumab:dexamethasone=1:153;
  ii. bevacizumab:dexamethasone=1:15.3;
  iii. bevacizumab:dexamethasone=1:1.53.

Figure 2B:
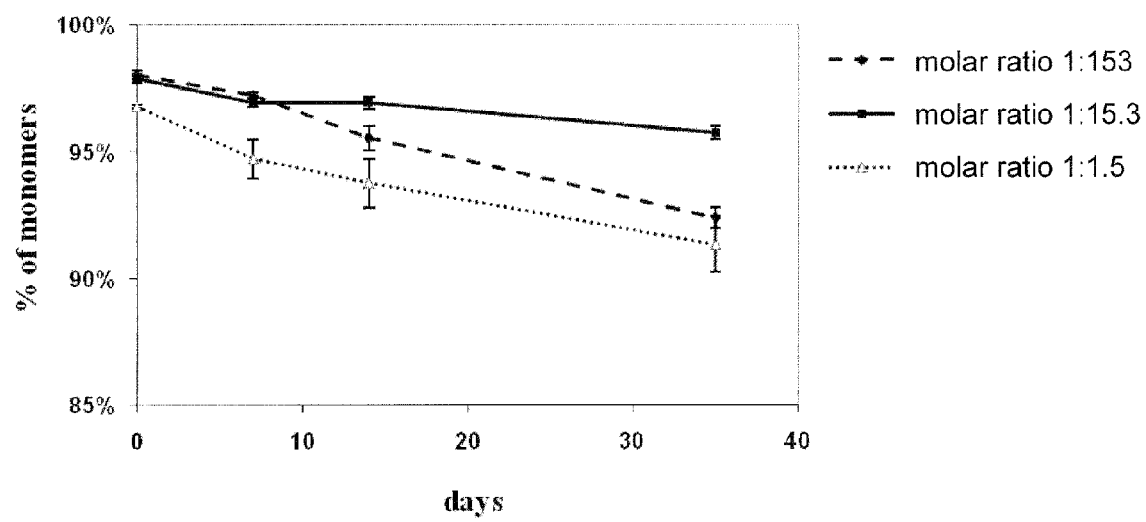
FIG. 2B shows the stabilizing effect of dexamethasone on bevacizumab, expressed in percentage of bevacizumab monomers, after combining bevacizumab with dexamethasone when stored at 40° C., pH 6.2, as described in Example 1. 2B: bevacizumab associated with dexamethasone at different bevacizumab:dexamethasone molar ratios; dashed line: 1:153, black line: 1:15.3, dotted line: 1:1.53.

All samples were stores at 40° C. during 35 days. Samples were analyzed directly after preparation (t0) and after 7, 14 and 35 days. The aggregation state of the antibodies was measured by multi-angle light scattering (MALS) after separation by asymmetrical flow field-flow fractionation (AFFF). The concentration of bevacizumab was determined by UV spectroscopy at 280 nm, based upon an extinction coefficient of 1.7 cm ml/mg. Data were collected and analysed with Astra software (Wyatt Technology Europe GmbH, Dembach, Germany). The aggregation state was expressed as the percentage of monomers versus time (FIG. 2B).

Further control experiments on the stability of bevacizumab alone were carried out: Concentration effect (5, 10, 18 and 25 mg/ml in 50 mM phosphate buffer pH 6.2) and effect of pH and storage temperature (pH 5 and pH 7 at 4° C., 25° C. and 40° C. during 35 days) on antibody stability.

Stability of Bevacizumab Alone

The stability of commercial product of bevacizumab is affected by an increase in pH, temperature or storage time as observed by the decrease of monomer percentage versus time of storage: At t=0, the average measured monomer percentage is 97.2±0.1% (n=6) and decreases to 94.7±0.2% after 7 days of storage and to 91.3±0.5% (n=6) after 35 days of storage at pH 6.2. After 35 days of storage, the percentage of monomers decreases to 96.9±0.2% (n=6) at 4° C., 96.6±0.1% (n=6) at 25 C.° and 91.3±0.5% (n=6) at 40° C. (FIG. 1A). This stability decrease versus time of storage is even more pronounced at higher pH (FIG. 1B) or higher bevacizumab concentrations: 98.1% (n=2) of bevacizumab is found to be monomer at a concentration of 5 mg/ml after 35 days at 40° C., compared to 97.2% (n=2) at 10 mg/ml, 92.9% (n=2) at 18 mg/ml and 92.8% (n=2) at 25 mg/ml. Therefore, bevacizumab aggregates are already present in the commercial product (pH 6.2) and an increase in its aggregation state over time storage, temperature storage and concentrations is observed.

Stability of Combined Compositions of Bevacizumab with Dexamethasone

Figure 1B:
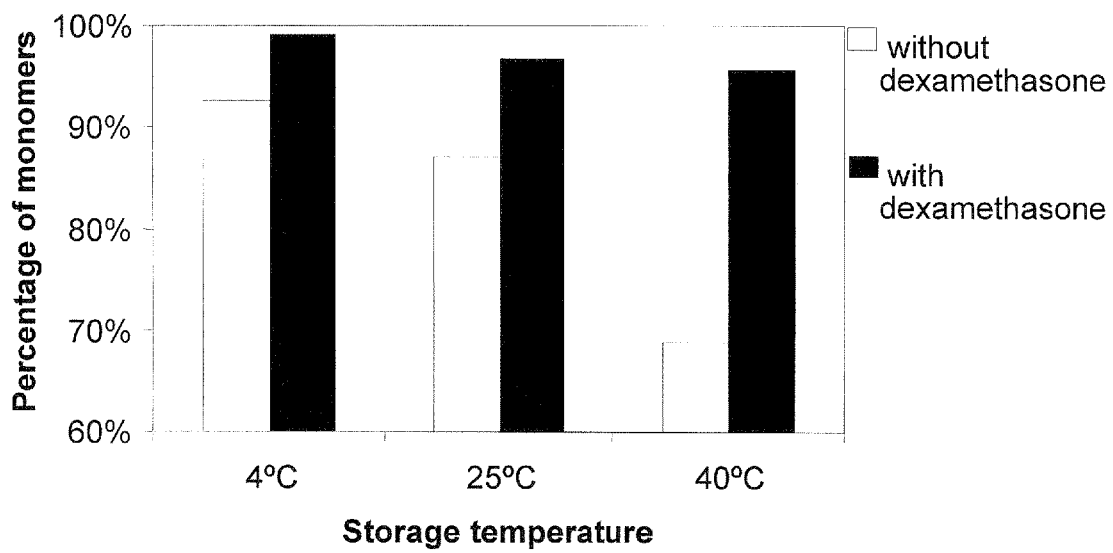

The association of bevacizumab with dexamethasone causes a surprising stabilization of the antibody in comparison with the sample of bevacizumab alone (FIGS. 1A & 1B). After 35 days of storage at 40° C. at pH 6.2 and pH 7.0, the combination sample shows average monomer percentages of 95.2% (n=2) for pH 6.2 and 95.6% (n=2) for pH 7.0 as compared to average monomer percentages of 87.5% (n=2) for pH 6.2 and 68.8% (n=2) for pH 7.0 for bevacizumab alone.

The percentage of monomers of bevacizumab with dexamethasone is still higher than 97% after about 15 days of storage at 40° C. at pH 6.2 (FIGS. 2A & 2B) at a molar ratio bevacizumab:dexamethasone=1:153 or after 35 days of storage at 40° C. at pH 6.2 (FIG. 2A) at a molar ratio bevacizumab:dexamethasone=1:15.3 (FIG. 2B).

These data clearly show that the combination of an intact antibody such as bevacizumab with a corticosteroid anti-inflammatory drug such as dexamethasone leads advantageously to stabilized antibody formulations.

Example 2

Comparison of the Stability of Bevacizumab Alone and in Combination with Betamethasone Phosphate Commercial formulation of bevacizumab (AVASTIN, Roche Pharma, Reinach, Switzerland) was dialysed overnight into 50 mM phosphate buffer pH 7.0. After dialysis, the bevacizumab formulation was stored for seven days at 40° C. to stress the antibody to induce aggregation of the antibody.

Betamethasone 21-phosphate disodium salt, purity≥97% (Sigma-Aldrich, Lausanne, Switzerland) was then added in two different concentrations, obtaining the following molar ratios:
  i. bevacizumab:betamethasone=1:153;
  ii. bevacizumab:betamethasone=1:15.3.

Both the antibody alone and the combined formulations were then stored stores at 40° C. during a further 28 days. Samples were analyzed directly before addition (t=0) and at 1, 7, 14 and 28 days after addition. The aggregation state of the antibodies was measured by multi-angle light scattering (MALS) after separation by asymmetrical flow field-flow fractionation (AFFF). The concentration of bevacizumab was determined by UV spectroscopy at 280 nm, based upon an extinction coefficient of 1.7 cm ml/mg. Data were collected and analysed with Astra software (Wyatt Technology Europe GmbH, Dernbach, Germany). The aggregation state was expressed as the percentage of monomers versus time (FIG. 3).

Figure 3:
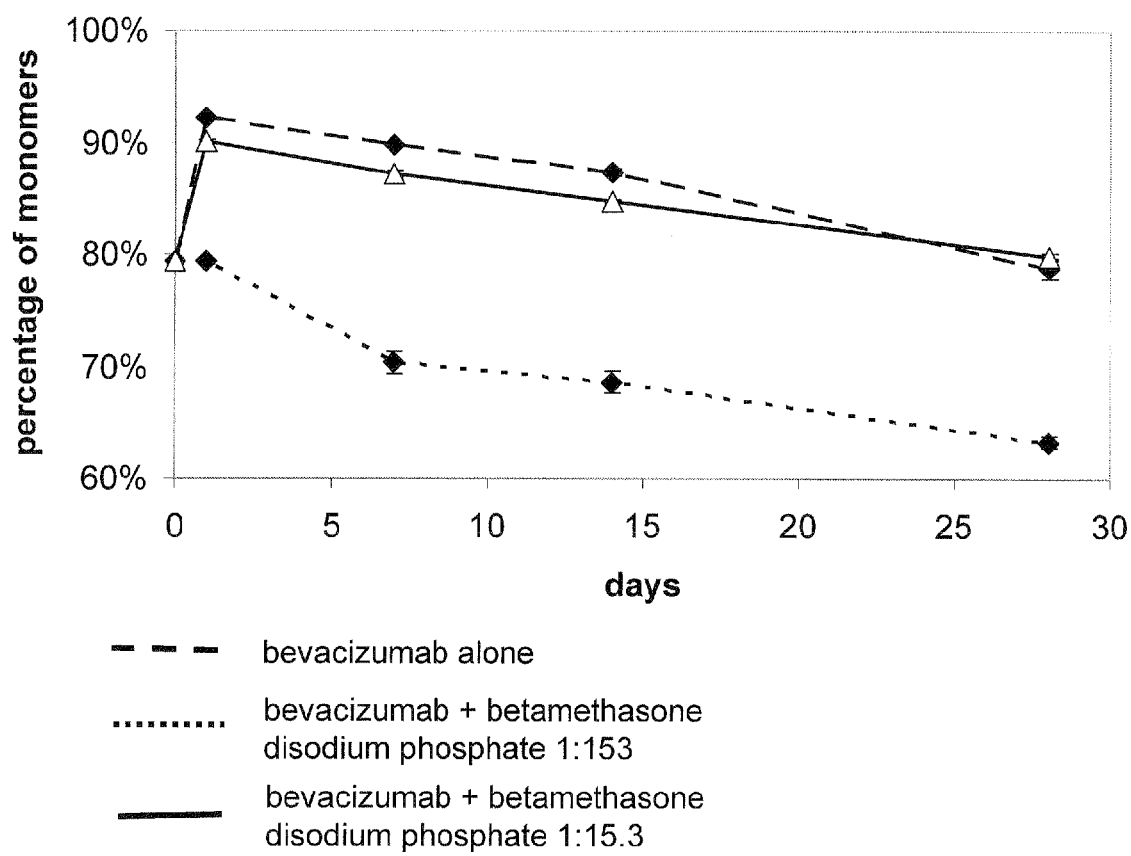
FIG. 3 shows the stabilizing effect of betamethasone on bevacizumab, expressed in percentage of bevacizumab monomers, after combining bevacizumab with betamethasone when stored at 40° C., pH 6.2, as described in Example 1. 2B: dotted line: bevacizumab alone; dashed line: bevacizumab combined with betamethasone at bevacizumab:betamethasone molar ratio 1:153; black line: bevacizumab combined with betamethasone at bevacizumab:betamethasone molar ratios 1:15.3.

Stability of Combined Compositions of Bevacizumab with Betamethasone Compared to Bevacizumab Alone The association of bevacizumab with betamethasone causes a surprising stabilization of the antibody in comparison with the sample of bevacizumab alone (FIG. 3). For the bevacizumab alone, at t=0, the average measured monomer percentage is 79.4±0.2% (n=3) and decreases to 70.3±0.9% (n=3) after 7 days of storage and to 63.2±0.5% (n=3) after 28 days of storage at pH 7.0. Therefore, considerable aggregation of bevacizumab is seen to occur on the initial storage at 40° C. over 7 days, and an increase in its aggregation state over time is observed.

Whereas for the combination examples, after 1 day of storage, the percentage of monomers in the combined formulations increases to 92.3±0.1% (n=3) at a molar ratio bevacizumab:betamethasone=1:153, and to 90.1±0.1% (n=3) at a molar ratio bevacizumab:betamethasone=1:15.3. Therefore addition of betamethasone is seen to lead to considerable reduction in the initial aggregation state of bevacizumab. Further, the percentage of monomers is still higher than 80% after 28 days of storage at 40° C. at pH 7.0 at a molar ratio bevacizumab:betamethasone=1:153 or 1:15.3 (FIG. 3).

These data clearly show that the combination of an intact antibody such as bevacizumab with a corticosteroid anti-inflammatory drug such as betamethasone leads advantageously to stabilized antibody formulations.

We claim:

1. A stable antibody formulation said formulation comprising an aqueous carrier, bevacizumab and a corticosteroid anti-inflammatory drug selected from dexamethasone, dexamethasone sodium phosphate, a dexamethasone derivative, betamethasone, betamethasone sodium phosphate, or a pharmaceutically acceptable salt thereof, wherein corticosteroid anti-inflammatory drug to bevacizumab-molar ratio ranges from is 1.53:1 to 153:1 and the dexamethasone derivative is of Formula (I):

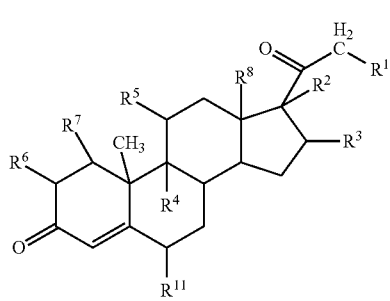

wherein $R^1$ is selected from H, halogen, —OH, —O$_4$PHNa$_2$, —O—C(O)—R$^9$; $R^2$ is selected from H, OH, —O—C(O)—R$^{10}$; $R^3$ is selected from H or —CH$_3$; $R^4$ is selected from H, and halogen; $R^5$ is selected from H, OH and carbonyl; $R^6$ and $R^7$ are H or form together a double bond; $R^8$ is selected from optionally substituted $C_1$-$C_6$ alkyl and optionally substituted acetyl; $R^9$ and $R^{10}$ are independently selected from optionally substituted $C_1$-$C_6$ alkyl and optionally substituted $C_3$-$C_8$-cycloalkyl; $R^{11}$ is selected from H or optionally substituted $C_1$-$C_6$ alkyl.

2. The formulation according to claim 1, wherein the formulation is a pharmaceutical formulation.

3. The formulation according to claim 1 wherein said corticosteroid anti-inflammatory drug is: a) dexamethasone or a derivative thereof; or b) betamethasone, wherein the dexamethasone derivative is of Formula (I):

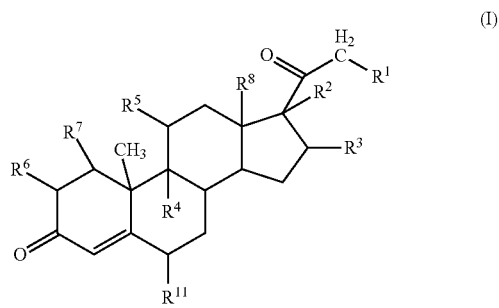

wherein $R^1$ is selected from H, halogen, —OH, —O$_4$PHNa$_2$, —O—C(O)—R$^9$; $R^2$ is selected from H, OH, —O—C(O)—R$^{10}$; $R^3$ is selected from H or —CH$_3$; $R^4$ is selected from H, and halogen; $R^5$ is selected from H, OH and carbonyl; $R^6$ and $R^7$ are H or form together a double bond; $R^8$ is selected from optionally substituted $C_1$-$C_6$ alkyl and optionally substituted acetyl; $R^9$ and $R^{10}$ are independently selected from optionally substituted $C_1$-$C_6$ alkyl and optionally substituted $C_3$-$C_8$-cycloalkyl; $R^{11}$ is selected from H or optionally substituted $C_1$-$C_6$ alkyl.

4. The formulation according to claim 3 wherein said corticosteroid anti-inflammatory drug is dexamethasone.

5. The formulation according to claim 3 wherein said corticosteroid anti-inflammatory drug is betamethasone.

6. The formulation according to claim 1 wherein the formulation has a pH in the range between pH 4.5 and pH 7.5.

7. The formulation according to claim 1, further comprising an excipient.

8. A pharmaceutical unit dosage form suitable for ocular administration to a mammal comprising an antibody formulation according to claim 1 in a suitable container.

9. A method of stabilizing bevacizumab in aqueous solution comprising combining bevacizumab with a corticosteroid anti-inflammatory drug, wherein said corticosteroid anti-inflammatory drug is selected from dexamethasone, dexamethasone sodium phosphate, a dexamethasone derivative, betamethasone, betamethasone sodium phosphate or pharmaceutically acceptable salts thereof, wherein the dexamethasone derivative is of Formula (I):

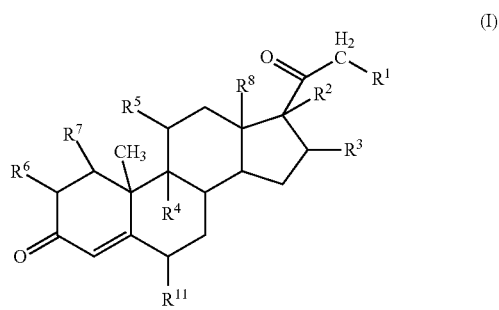

wherein $R^1$ is selected from H, halogen, —OH, —O$_4$PHNa$_2$, —O—C(O)—R$^9$; $R^2$ is selected from H, OH, —O—C(O)—R$^{10}$; $R^3$ is selected from H or —CH$_3$; $R^4$ is selected from H, and halogen; $R^5$ is selected from H, OH and carbonyl; $R^6$ and $R^7$ are H or form together a double bond; $R^8$ is selected from optionally substituted C$_1$-C$_6$ alkyl and optionally substituted acetyl; $R^9$ and $R^{10}$ are independently selected from optionally substituted C$_1$-C$_6$ alkyl and optionally substituted C$_3$-C$_8$-cycloalkyl; $R^{11}$ is selected from H or optionally substituted C$_1$-C$_6$ alkyl and the corticosteroid anti-inflammatory drug to bevacizumab molar ratio ranges from 1.53:1 to 153:1.

10. The method according to claim 9 wherein said corticosteroid anti-inflammatory drug is dexamethasone or a derivative thereof.

11. The method according to claim 10 wherein the corticosteroid anti-inflammatory drug is betamethasone.

12. A process for the preparation of a bevacizumab formulation comprising the steps of:
   (i) combining bevacizumab with a corticosteroid anti-inflammatory drug into a liquid mixture or forming a formulation comprising bevacizumab and a liquid medium containing a corticosteroid anti-inflammatory drug, said corticosteroid anti-inflammatory drug selected from dexamethasone, dexamethasone sodium phosphate, a dexamethasone derivative, betamethasone, betamethasone sodium phosphate or pharmaceutically acceptable salts of and wherein the dexamethasone derivative is of Formula (I):

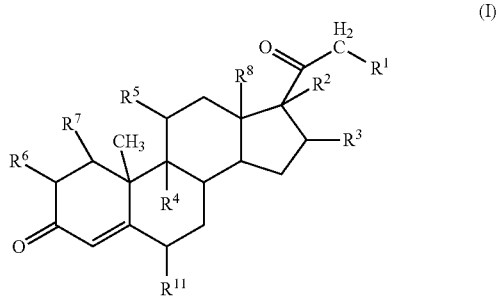

wherein $R^1$ is selected from H, halogen, —OH, —O$_4$PHNa$_2$, —O—C(O)—R$^9$; $R^2$ is selected from H, OH, —O—C(O)—R$^{10}$; $R^3$ is selected from H or —CH$_3$; $R^4$ is selected from H, and halogen; $R^5$ is selected from H, OH and carbonyl; $R^6$ and $R^7$ are H or form together a double bond; $R^8$ is selected from optionally substituted C$_1$-C$_6$ alkyl and optionally substituted acetyl; $R^9$ and $R^{10}$ are independently selected from optionally substituted C$_1$-C$_6$ alkyl and optionally substituted C$_3$-C$_8$-cycloalkyl; $R^{11}$ is selected from H or optionally substituted C$_1$-C$_6$ alkyl and the corticosteroid anti-inflammatory drug to bevacizumab molar ratio ranges from 1.53:1 to 153:1; and formulation obtained under step (i.

13. The process according to claim 12 wherein said corticosteroid anti-inflammatory drug is dexamethasone or a derivative thereof.

14. The process according to claim 13 wherein said corticosteroid anti-inflammatory drug is betamethasone.

15. A method of inhibiting the biological activity of vascular endothelial growth factor (VEGF) in a subject comprising administering to a subject having a disease or a disorder selected from a cancer, a neovascular age-related macular degeneration disease (AMD) and a disorder associated with AMD a therapeutically effective amount of a stable antibody formulation according to claim 1.

16. The stable antibody formulation according to claim 1, wherein less than 10% of antibody in said formulation forms an aggregate during storage at 40° C. for 35 days, as determined by multi-angle light scattering (MALS) coupled to asymmetrical flow field-flow fractionation (AFFF).

17. The stable antibody formulation according to claim 16, wherein said formulation comprises bevacizumab and dexamethasone.

18. The stable antibody formulation according to claim 1, wherein the corticosteroid anti-inflammatory drug is at a concentration in the range of about 0.1 mg/ml to about 13 mg/ml.

19. The stable antibody formulation according to claim 1, wherein bevacizumab is at a concentration in the range of about 5 mg/ml to about 100 mg/ml.

* * * * *